United States Patent [19]
Gavin et al.

[11] Patent Number: 5,962,250
[45] Date of Patent: Oct. 5, 1999

[54] SPLIT MULTI-WELL PLATE AND METHODS

[75] Inventors: Robert M. Gavin, San Jose; Harold E. Selick, Belmont; Gregory A. Smith, Union City, all of Calif.

[73] Assignee: Glaxo Group Limited, Greenford, United Kingdom

[21] Appl. No.: 08/959,434

[22] Filed: Oct. 28, 1997

[51] Int. Cl.$^6$ .............................. C12Q 1/02; C12M 3/00
[52] U.S. Cl. ........................ 435/29; 422/101; 422/102; 435/395; 435/401; 435/420; 435/297.5; 435/288.4; 435/305.2
[58] Field of Search ................... 422/101, 102; 435/297.5, 288.4, 288.5, 305.1, 305.2, 29, 395, 401, 420

[56] References Cited

U.S. PATENT DOCUMENTS

| | | |
|---|---|---|
| 4,871,674 | 10/1989 | Matsui et al. . |
| 5,026,649 | 6/1991 | Lyman et al. . |
| 5,028,541 | 7/1991 | Kiel et al. . |
| 5,068,195 | 11/1991 | Howell et al. . |
| 5,089,385 | 2/1992 | Kiel et al. . |
| 5,139,946 | 8/1992 | Howell et al. . |
| 5,183,760 | 2/1993 | Sweetana et al. . |
| 5,409,829 | 4/1995 | Mussi et al. . |
| 5,468,638 | 11/1995 | Barker et al. . |
| 5,490,415 | 2/1996 | Mak et al. . |
| 5,510,262 | 4/1996 | Stephanopoulos et al. . |
| 5,583,037 | 12/1996 | Mussi et al. ............... 435/240.241 |
| 5,591,636 | 1/1997 | Grass . |
| 5,599,688 | 2/1997 | Grass . |

FOREIGN PATENT DOCUMENTS

| | | | |
|---|---|---|---|
| WO 94/06902 | 3/1994 | WIPO | ............................ C12M 3/06 |
| WO 97/06890 | 2/1997 | WIPO | ............................ B01L 3/00 |

OTHER PUBLICATIONS

Ubeira et al. (1993), "A new cell culture method (the lateral diffusion system) suitable for the induction of antibody–forming cells in vitro," J. Immunol. Methods 159:107–113.

*Primary Examiner*—David A. Redding
*Attorney, Agent, or Firm*—Darin Gibby; Lauren L. Stevens

[57] ABSTRACT

The invention provides exemplary testing devices, systems, and methods for evaluating the permeation of various chemicals through different types of cells. In one exemplary embodiment, a testing device is provided which comprises a plate defining at least one well having an open top end. At least one membrane is insertable into the well in a generally vertical orientation to divide the well into separate chambers. The membrane is removable from the well to allow the cells to be grown on the membrane before insertion into the well.

23 Claims, 10 Drawing Sheets

SPLIT MULTI-WELL PLATE AND METHODS

BACKGROUND OF THE INVENTION

This invention relates generally to the field of testing systems and methods, and more particularly to systems and methods for transport or permeation testing. In one particular aspect, the invention provides systems and methods for culturing cells onto a membrane and then using the membrane to simulate an epithelial cell layer, such as the cells which form the inner lining of a human intestine or blood vessel. In this way, transport or permeation tests may be performed using the membrane.

In humans, ingested food passes from the stomach to the small intestine where proteins, fats, carbohydrates and other nutrients are absorbed and distributed into circulation for use in various organs and cells throughout the body. The small intestine is about five to six meters in length and has an extremely large surface area for absorbing nutrients and other materials. The interior of the small intestine includes the mucosal epithelium which comprises small fingerlike projections called villi which protrude into the intestine and provide the nutrient absorption surface.

For a variety of reasons, it is desirable to study and evaluate how various chemicals which are orally ingested into a human will be absorbed into the blood stream through the intestinal wall. Such evaluation can be useful in, for example, drug testing to determine how various drugs will be absorbed into the blood stream. Transport of various substances through other types of epithelial cells can also be useful in therapeutically treating patients.

In order to evaluate how certain chemicals or substances will permeate epithelial cells, some have proposed growing mammalian-based cells on a membrane which in turn is used to mimic a cell layer within the body. To properly culture the cells on the membrane, it is usually best to have the membrane horizontally oriented when seeding the cells on the membrane. Hence, some previously proposed testing systems comprise a cup having a membrane at its bottom end. In this way, cells may be seeded on the membrane while the membrane is horizontally oriented. After the cells have grown onto the membrane, the cup is inserted into a larger well and various chemicals are placed into the cup to evaluate how the chemicals will permeate the cells on the membrane and into fluid in the larger well.

Such testing systems suffer from a variety of drawbacks, including limited access to both sides of the membrane, particularly since the bottom side of the membrane will be enclosed by the well into which the cup is inserted. Another drawback is the significant amount of time required to separately seed the cells into each of the walls. A further drawback to such systems is their limited use in accommodating smaller sized membranes. For example, many multi-well plates are being provided with increased numbers of wells whose dimensions are significantly smaller to create larger densities of wells within the plates. Accordingly, each membrane needs to be made smaller in order to fit within the smaller wells. However, when reducing the size of the membranes with the testing systems described above, the membrane's surface area may be too small to provide an adequate transport interface. In turn, this can lower concentrations or transported amounts to levels which restrict analytical methodologies presently available to quantify results. Further, the activity provided by a cell layer on such small membrane sizes may not be representative of the activity provided by a cell layer on a larger membrane.

Hence, for these and other reasons, it would be desirable to provide systems and methods which will allow cells to be seeded horizontally in an efficient manner. In some cases it would also be desirable to allow access to both sides of the membrane during a testing procedure. Further, it would be desirable to provide a design for a testing system where membrane densities are greatly increased while still being sufficiently sized to effectively accommodate cell growth and to provide an adequate transport interface.

SUMMARY OF THE INVENTION

The invention provides systems, devices and methods that are useful in performing various transport or permeation tests, preferably in order to simulate the transport of various substances through epithelial cell layers, such as the cells which line the human intestine, blood vessels, and the like. In one exemplary embodiment, the invention provides a testing device which comprises a plate defining at least one well. At least one membrane is provided which is insertable into the well to divide the well into separate chambers. The membrane is removable from the well to allow cells to be grown on the membrane before insertion into the well. With this arrangement, the membrane may be horizontally oriented to allow cells to be seeded on the membrane. Subsequently, the membrane may be inserted into the well and permeation tests performed.

In one exemplary aspect, the device further includes a divider to which the membrane is operably attached. The divider is insertable into the well to hold the membrane in a generally vertical orientation within the well. In this way, the transport interface between the chambers is maximized to in turn maximize transport between the chambers. Although a generally vertical orientation is preferred, it will be appreciated that in some cases the membrane may be inclined or even horizontal.

Preferably, the divider is arranged so that it encompasses a periphery of the membrane. Further, the divider will preferably form a raised edge around the periphery of the membrane to constrain cell growth to the membrane. In one particular aspect, the divider comprises a half-well having a planar face to which the membrane is operably attached. In this manner, the half-well may be inserted into the well to divide the well into separate chambers.

In still a further aspect, the plate defines a plurality of wells, and a plurality of membranes are provided which are insertable into the wells in a generally vertical orientation. The vertical arrangement of the membranes in this manner is advantageous in that large numbers of wells may be provided within a single plate, with each membrane being sufficiently sized so that the cells may be properly cultured thereon prior to insertion.

In one particular aspect, the divider comprises a plurality of teeth to which the membranes are operably attached. A bridge is further provided to interconnect the teeth. In this way, the teeth may be inserted into a row of wells to place a separate membrane into each well. In an alternative aspect, the divider comprises an elongate member to which the membranes are operably attached. With this arrangement, the plate preferably includes an elongate slot extending between the array of wells. In this way, the elongate member may be inserted into the slot to place the membranes into the wells. In still a further alternative aspect, the divider comprises a plurality of half-wells, each having a planar face to which the membranes are operably attached. The half-wells are insertable into the wells to place the membranes into the wells. Preferably, the halfwells will be operably attached to each other to create a strip of half-wells.

In still a further aspect, the wells are arranged in a two-dimensional array of rows and columns. With this configuration, a plurality of row dividers are provided, each having a plurality of membranes operably attached thereto. In this way, each row may have its wells divided by inserting the dividers into the rows. In another aspect, the membrane is constructed from materials such as polytetrafluroethylene, polyethylene, PET, polycarbonate and the like.

In another exemplary embodiment, the invention provides a testing system which comprises at least one membrane and a cell culture device having cells therein. In this way, the membrane may be placed into the cell culture device in a horizontal orientation to allow the cells to be seeded on the membrane. The system further includes a plate having at least one test well into which the membrane may be inserted after cells have been grown on the membrane. In this way, the membrane divides the well into separate chambers so that various tests may be performed.

In one particular aspect, the cells within the cell culture device comprise mammalian-based cells. In another aspect, the system further includes a means for measuring the concentration of a substance within each chamber after the substance has been placed into one of the chambers and has diffused into the other chamber. In this way, the permeation rate of the substance through the membrane may be determined. In still another aspect, a means is provided for introducing the substance into the well after placement of the membrane into the well. The system may further include a variety of dividers as described above which are insertable into the well to hold the membrane in a generally vertical or inclined orientation within the well.

In still another embodiment, an exemplary testing system is provided which comprises a base member having a plurality of wells. A top member is also provided having a plurality of apertures, with at least some of the apertures corresponding to the wells of the base member. A membrane sheet is further provided to receive a layer of cells and to be placed between the top member and the bottom member. In this way, a substance that is placed within the apertures may permeate through the membrane and into the wells. Such a system is therefore advantageous in that the membrane sheet may be separated from the system to allow the cells to be grown on the membrane. The membrane sheet may then be placed between the base member and the top member to facilitate a testing procedure.

Optionally, a gasket may be provided and be placed between the base member and the top member to provide a seal between the top member and the base member. In another aspect, a securing mechanism may be provided to secure the top member to the base member. Preferably, the cells grown on the membrane sheet will comprise monolayers of mammalian based cells.

The invention still further provides an exemplary method for performing assays. According to the method, cells are grown onto a membrane. The membrane is then inserted into a well to divide the well into a donor chamber and a receptor chamber. At least one substance is then introduced into the donor chamber and is allowed to diffuse through the membrane into the receptor chamber. A characteristic of the substance that is within the donor chamber and the receptor chamber is then evaluated over time.

In a preferable aspect, the evaluated characteristic is the concentration of the substance. In this way, the permeation rate of the substance through the cells on the membrane may be determined based at least in part on the measured concentrations of the substance within the donor chamber and the receptor chamber. To facilitate evaluation, the substance preferably comprises a chemical which is introduced into a buffer solution within the chambers.

In one particularly preferable aspect, the cells are seeded onto the membrane while the membrane is in a generally horizontal orientation. Such a horizontal orientation is particularly useful when the cells comprise mammalian-based cells. Further, to facilitate growth of the cells the surface area of the membrane may be framed to constrain growth of the cells onto the membrane.

In another particular aspect, the membrane is operably attached to a divider and the divider is inserted into the well in a generally vertical orientation. In one aspect, the well includes at least one generally vertically oriented slot into which the divider is slid to insert the divider into the well. In an alternative aspect, the divider comprises a half-well having a planar face to which the membrane is operably attached. In this way, the half-well is inserted into the well.

In a further aspect, the plate defines an array of wells, and the divider includes a plurality of membranes. After the cells have been grown onto the membrane, the divider is inserted into the wells in a generally vertical orientation so that each well includes one of the membranes. In this way, the number of wells may be greatly increased, each having an appropriate cell layer to divide the wells into separate chambers. In one aspect, the divider comprises a plurality of teeth to which the membranes are operably attached. A bridge is provided to interconnect the teeth and may be grasped to insert the teeth into the array of wells. Alternatively, the divider may comprise an elongate member to which the membranes are operably attached.

In a further alternative, the divider comprises a plurality of half-wells which have a planar face to which the membranes are operably attached. Each of the dividers are configured so that they may be horizontally oriented to allow cells to be seeded on each of the membranes. The dividers may then be inserted into the wells in a vertical orientation.

The invention still further provides another exemplary method for performing assays. According to the method, a base member is provided having a plurality of wells. A top member is also provided and includes a plurality of apertures. In the method, cells are grown on to a membrane sheet which in turn is placed between the base member and the top member. The top member is secured to the base member such that at least some of the wells are aligned with at least some of the apertures. A substance is then introduced into the aligned apertures and is allowed to permeate the membrane sheet. A characteristic of the substance within the wells is then evaluated.

The evaluated characteristic can comprise the concentration of the substance. Based on the measured concentration, a permeation rate of the substance through the membrane sheet may then be determined. In one optional aspect, the wells may be filled with a buffer solution prior to placement of the membrane sheet between the top member and the base member. In another aspect, the substance may be maintained within a desired temperature range while permeating the membrane sheet. One particularly advantageous feature of the method is that the membrane sheet may be either horizontally oriented or vertically oriented during permeation. To facilitate evaluation of the characteristic, the membrane sheet may be removed from the base layer or may be punctured to gain access to the substance within the wells.

DETAILED DESCRIPTION OF THE SPECIFIC EMBODIMENTS

Figure 1:
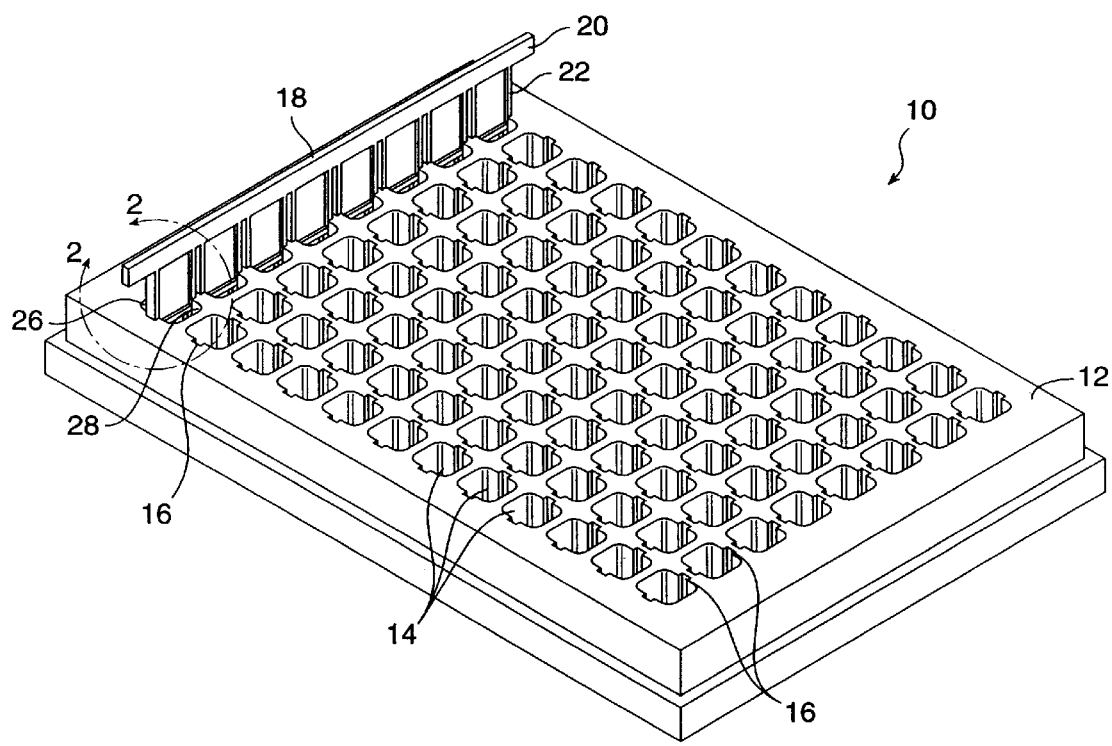
FIG. 1 is a perspective view of an exemplary testing device according to the invention.

The invention provides systems, devices and methods for testing and evaluating the transport or permeation of various substances through a layer of cells, and particularly epithelial cell layers, including those found in blood vessels throughout the body, arteries, the intestine, and the like. Although useful in a wide variety of simulation applications, the invention will find use in modelling intestinal permeation of drug-like compounds.

According to the invention, mammalian-based cells are seeded on a membrane while the membrane is in a generally horizontal orientation. Such an orientation is preferably employed to facilitate attachment of the mammalian-based cells to the membrane. The membrane is then inserted into the wells of a multi-well plate, preferably in a generally vertical orientation, to divide the wells into separate chambers, such as a receptor chamber and a donor chamber. In some cases, however, it may be desirable to have the membrane inserted horizontally or at an incline. Vertical orientation of the membrane is advantageous in that it allows for a more efficient use of the space within the wells. In this way, a larger membrane surface may be provided to enhance the sensitivity of the system. Further, by optimizing the size of the membrane, smaller well sizes may be used while still providing an adequate transport interface. Once the membrane is inserted, various substances may be introduced into the donor chambers where they will permeate through the cells on the membrane into the receptor chambers. The permeation rate may be determined by measuring the concentration levels over time in both the donor chambers and the receptor chambers. In this way, a scientist will be able to evaluate the permeation of various substances through the cells in order to model how the human body will absorb such substances.

The system of the invention will preferably employ a cell culture device which maintains cells in a tissue culture media until the cells are ready to be seeded onto the membrane. Preferably, the cells will be mammalian-based cells and the membrane will preferably be constructed of a porous material, such as polytetrafluroethylene (commonly referred to as teflon), polyethylene, PCT, polycarbonate, or the like. For convenience of handling, the membranes will preferably be operably attached to a divider. In addition to facilitating handling of the membranes, the divider will preferably also encompass or frame the periphery of the membranes with a raised edge to constrain the growth of the cells to the membrane. In this way, growth of the mammalian-based cells onto the membrane will be facilitated. Use of such a divider is further advantageous in that it may be employed to horizontally orient the membranes when growing the cells on the membrane.

According to some embodiments, once a sufficient number of cells have been seeded onto the membranes, the divider may be removed from the cell culture device and placed into the wells of a multi-well plate. Exemplary plates which may be used with the invention comprise conventionally formatted multi-well plates, including 96-well plates, 384-well plates, and the like. Such multi-well plates may be "off the shelf" type plates or may be adapted to facilitate receipt of the divider depending on the particular configuration of the divider as described in greater detail hereinafter. Configuration of the membranes onto a removable divider as described herein is particularly advantageous in that the cells may more efficiently be seeded into the membrane. Further, by vertically orienting the membranes in the wells, the surface area of the membranes is maximized to more effectively accommodate growth of mammalian-based cells. Moreover, such vertical orientation maximizes the transport interface to allow the membranes to be used within the relatively small wells of dense multi-well plates.

Either prior to or following insertion of the membranes into the wells, both the donor chambers and the receptor chambers will preferably be filled with a buffer solution. A variety of substances may then be introduced into the donor chambers where they will diffuse through the membranes and into the receptor chambers. Exemplary substances which may be introduced into the donor chambers include a wide variety of drug compounds, chemicals, and the like.

To facilitate introduction of such substances, the invention will preferably include a fluid delivery device, such as a pipette or multi-channel pipette. This may be done in an automated or manual manner. Following introduction of the substances into the donor chambers, various concentration measurements will be taken over time in both the donor chambers and receptor chambers to determine the permeation rate of the particular substance through the cells. The particular concentration may be evaluated using commercially available measuring equipment, such as an HPLC, a fluorescent plate reader, an absorbance plate reader, and the like.

Figure 2:
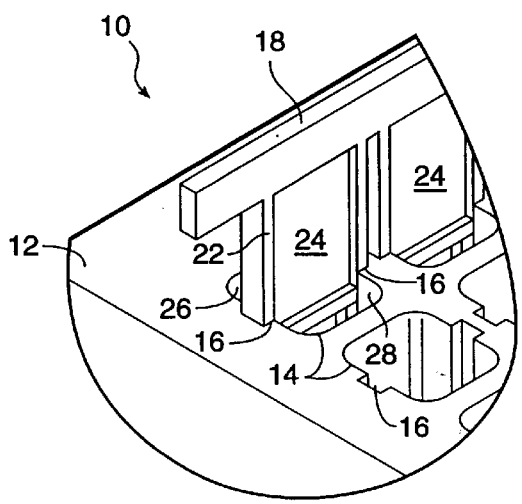
FIG. 2 is a more detailed view of the device of FIG. 1 taken along lines 2—2.
Figure 3:
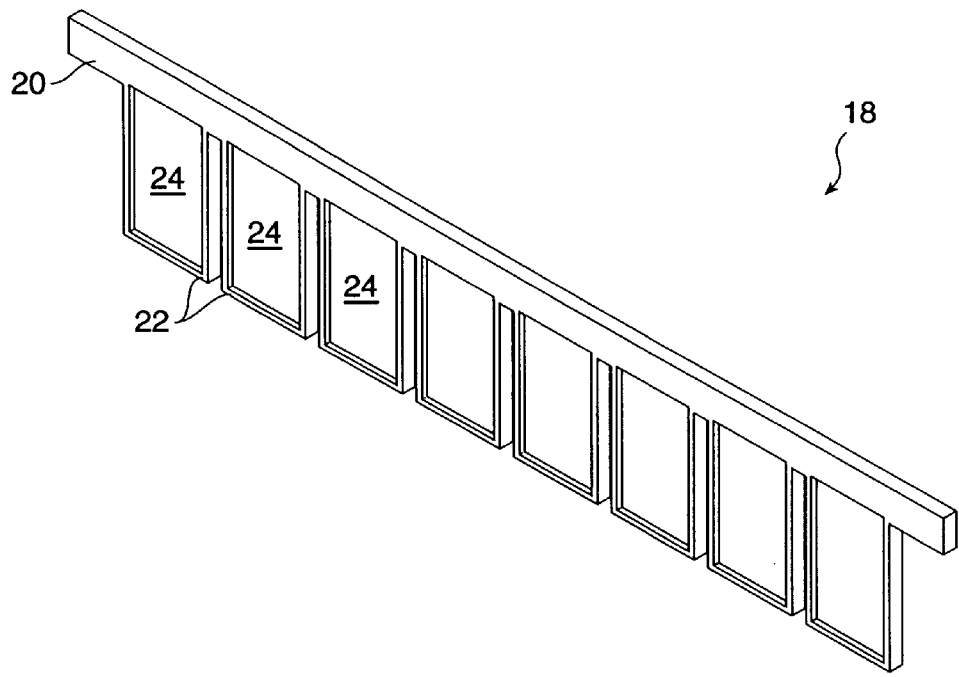
FIG. 3 is a perspective view of a divider of the tester of FIG. 1 having a plurality of membranes for dividing wells into separate chambers.

Referring now to FIGS. 1—3, an exemplary embodiment of a testing device 10 will be described. Device 10 comprises a plate 12 having a plurality of wells 14. Each well 14 includes an open top end and a pair of grooves 16 which are vertically oriented when plate 12 rests upon a horizontal surface. As shown, plate 12 includes 96 wells. However, it will be appreciated that plate 12 may be provided with larger or smaller numbers of wells. Further, wells 14 may be organized into a two-dimensional array as shown or in other configurations.

Testing device 10 further comprises a divider 18 having a bridge 20 and a plurality of teeth 22. As best shown in FIGS. 2 and 3, each tooth 22 defines a central opening to which a membrane 24 is attached. With this configuration, divider 18 may be inserted into a row of the wells as shown, with teeth 22 sliding within grooves 16 to vertically orient membranes 24 within wells 16 and to divide each well into a receptor chamber 26 and a donor chamber 28. Hence, divider 18 is advantageous in that it may be removed from testing device 10 so that cells may be grown on membranes 24 while the membranes are in a horizontal orientation. After a layer of cells has grown on membranes 24, divider 18 may be inserted into a row of wells 14 to divide the wells and to place the membranes in a vertical orientation. A substance, such as a chemical or drug, may then be placed into donor chamber 28 where it will diffuse through membrane 24 and into receptor chamber 26. Concentration measurements may then be taken in both the receptor chamber 26 and donor chamber 28 to determine the permeation rate of the substance through the cells on membrane 24.

The surface area of membrane 24 may vary depending upon a variety of factors, including the size of wells 14, the type of cells being used, the analytical techniques available to measure the amount of material transported, and the like. The surface area should be large enough so that it will adequately model a desired cell layer. To assist in growing the cells on membrane 24, teeth 22 will preferably define a raised edge which encompasses the periphery of membrane 24. Exemplary materials for constructing membrane 24 comprise polytetrafluroethylene, polyethylene, PET, polycarbonate, and the like.

Plate 12 will preferably have overall dimensions which are similar to those used with commercially available 96-well plates so that plate 12 may be used with commercially available processing equipment. However, it will be appreciated that as denser plates become more commercially accepted, divider 18 may be modified to accommodate more teeth and membranes so as to be useful with denser plate designs.

Figure 4:
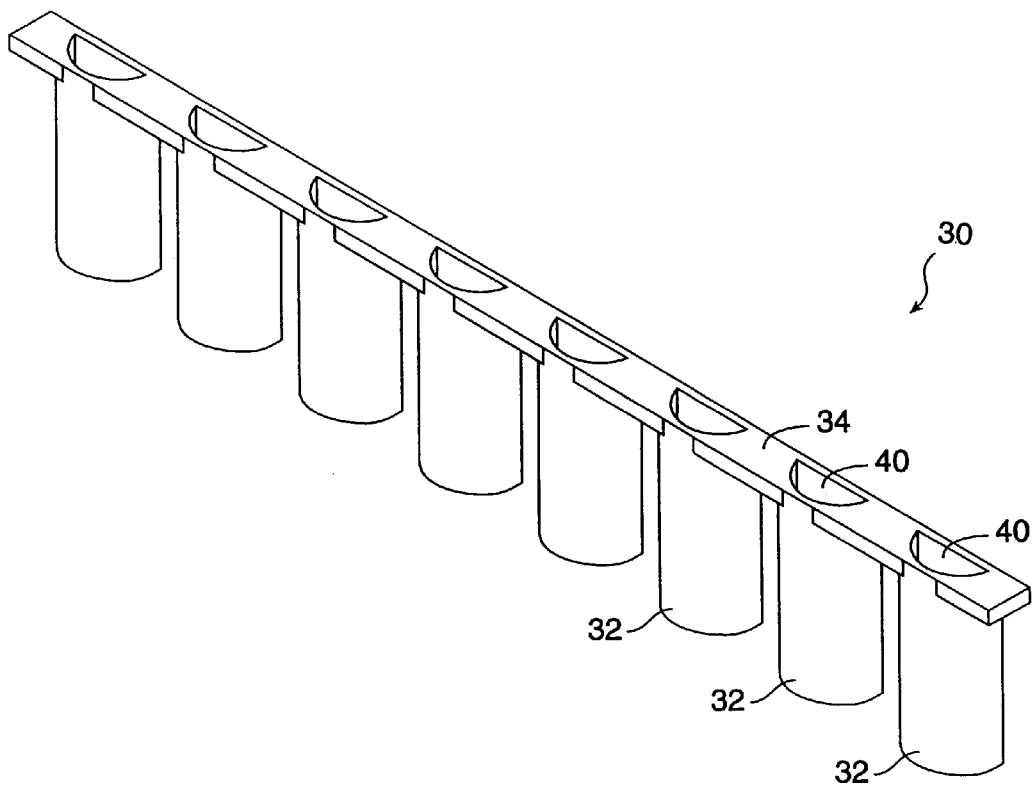
FIG. 4 is a top perspective view of a strip of half-wells for dividing the wells of a multi-well plate into separate chambers when inserted therein according to the invention.
Figure 5:
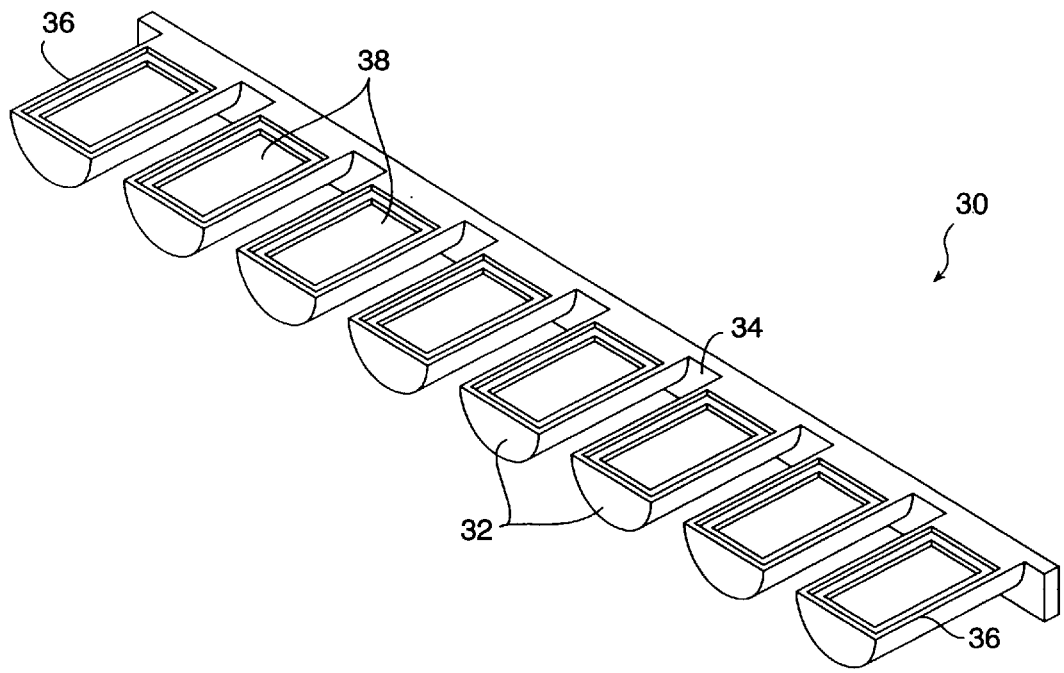
FIG. 5 is a bottom perspective view of the strip of half-wells of FIG. 4 showing a membrane attached to each halfwell.

Referring to FIGS. 4 and 5, an alternative embodiment of a divider 30 will be described. Divider 30 comprises a plurality of half-wells 32 which are connected by a strip 34. Half-wells 32 include a planar face 36 which each define an opening over which a membrane 38 is attached. Face 36 preferably defines a raised edge around membranes 38 similar to divider 18 as previously described.

Divider 30 is configured to be inserted into the wells of a conventional multi-plate well. As shown, divider 30 includes eight half-wells which may be inserted into a row of wells of a conventional 96-well plate. Alternatively, fewer or more half-wells may be provided for insertion into different configurations of multi-well plates. When divider 30 is inserted into a row of wells, each well is divided into a donor chamber 40 (defined by the half-well) and a receptor chamber (not shown). In this way, various substances may be diffused through membranes 38 to determine the absorption by the cells on the membrane similar to the embodiment previously described in connection with FIG. 1. Likewise, divider 30 is removable from the multi-well plate so that cells may be grown on membranes 38 while in a generally horizontal orientation. When inserted into wells of a multi-well plate, the half-well design will orient membranes 38 in a generally vertical orientation.

Figure 6:
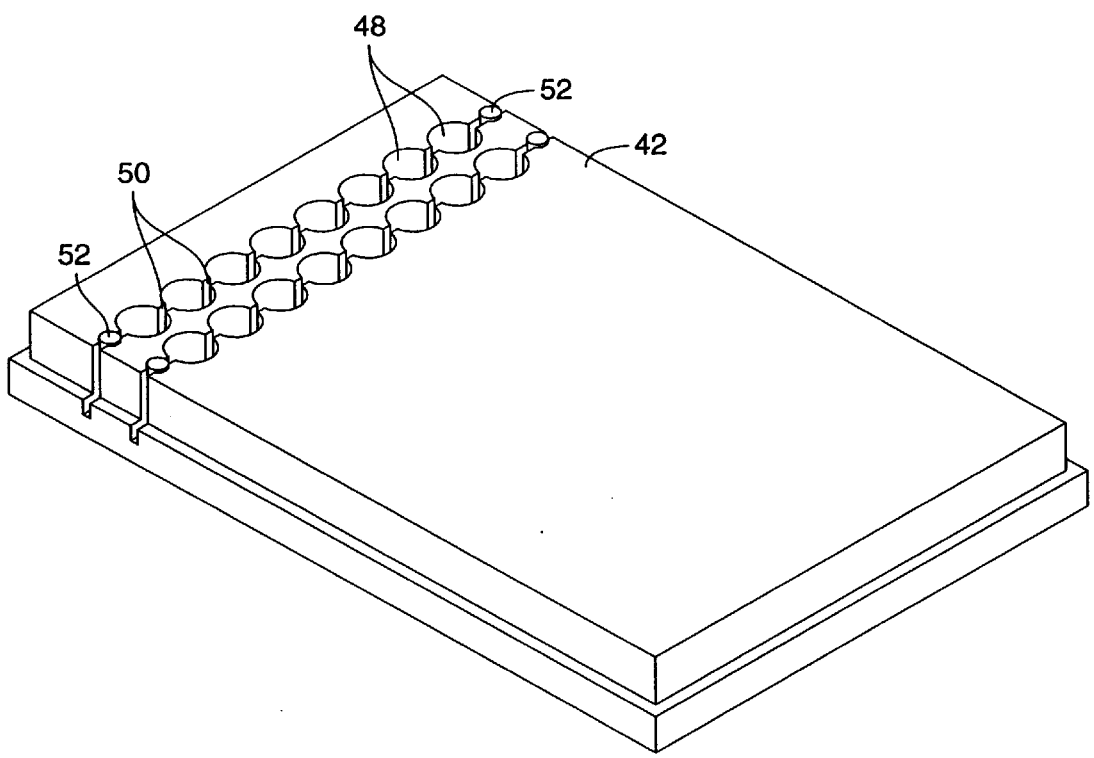
FIG. 6 is a top perspective view of an embodiment of a multi-well plate having an elongate slot extending through each row of wells according to the invention.
Figure 7:
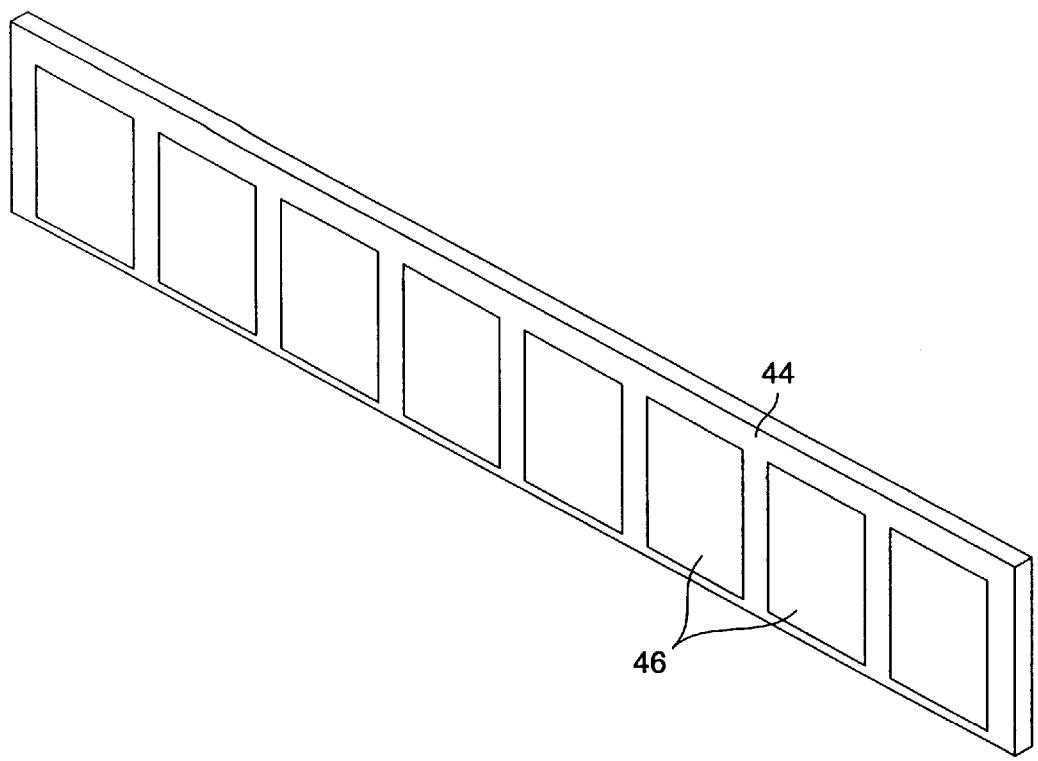
FIG. 7 is a top perspective view of a divider having a plurality of membranes which may be inserted into one of the slots of the plate of FIG. 6 according to the invention.

Referring now to FIGS. 6 and 7, an alternative testing device will be described which comprises a multi-well plate 42 (see FIG. 6) and a divider 44 having a plurality of membranes 46 (see FIG. 7). Plate 42 includes a plurality of wells 48 which are similar to wells of commercially available multi-well plates (only two rows of wells are illustrated for purposes of convenience). Extending between each row of wells is an elongate slot 50. Pins 52 are provided at each end of slot 50 to assist in sliding dividers 44 into the correct location so that the membranes are correctly positioned in the wells without damaging the membranes. Slot 50 is adapted to receive divider 44 so that each membrane 46 divides each well 48 into a receptor chamber and a donor chamber similar to the embodiments previously described. As with other embodiments, divider 44 will preferably define raised edges around membranes 46 to constrain cell growth to the membranes.

Figure 8:
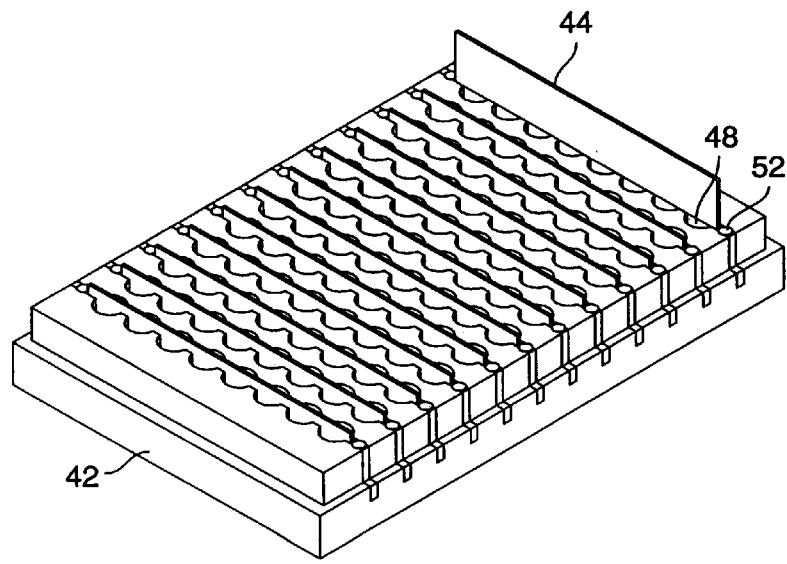
FIG. 8 is a top perspective view of the plate of FIG. 6 showing the divider of FIG. 7 being inserted into one of the slots according to the invention.
Figure 9:
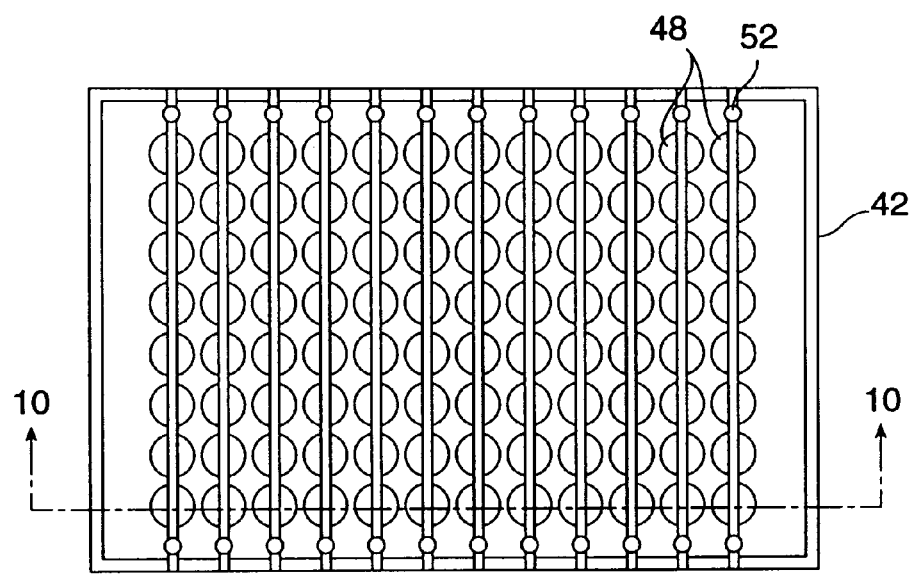
FIG. 9 is a top plan view of the plate of FIG. 8 having dividers inserted in each row.
Figure 10:
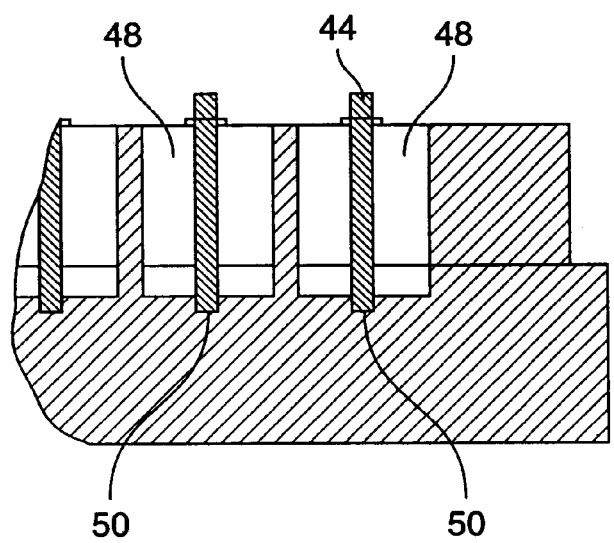
FIG. 10 is a partial cross-sectional view of the plate of FIG. 9 taken along lines 10—10.

Insertion of divider 44 into slots 50 is best illustrated in FIGS. 8–10. As shown, each row of wells receives a separate divider 44 so that each well 48 will be divided into a receptor chamber and a donor chamber. As shown in FIG. 10, slot 50 extends below the bottom surface of each well 48 to prevent fluids from leaking around divider 44. Further, divider 44 will preferably be configured so that a seal will be created between divider 44 and plate 42 when divider 44 is inserted into slot 50. In this way, liquids will be prevented from seeping into adjacent wells.

Figure 11:
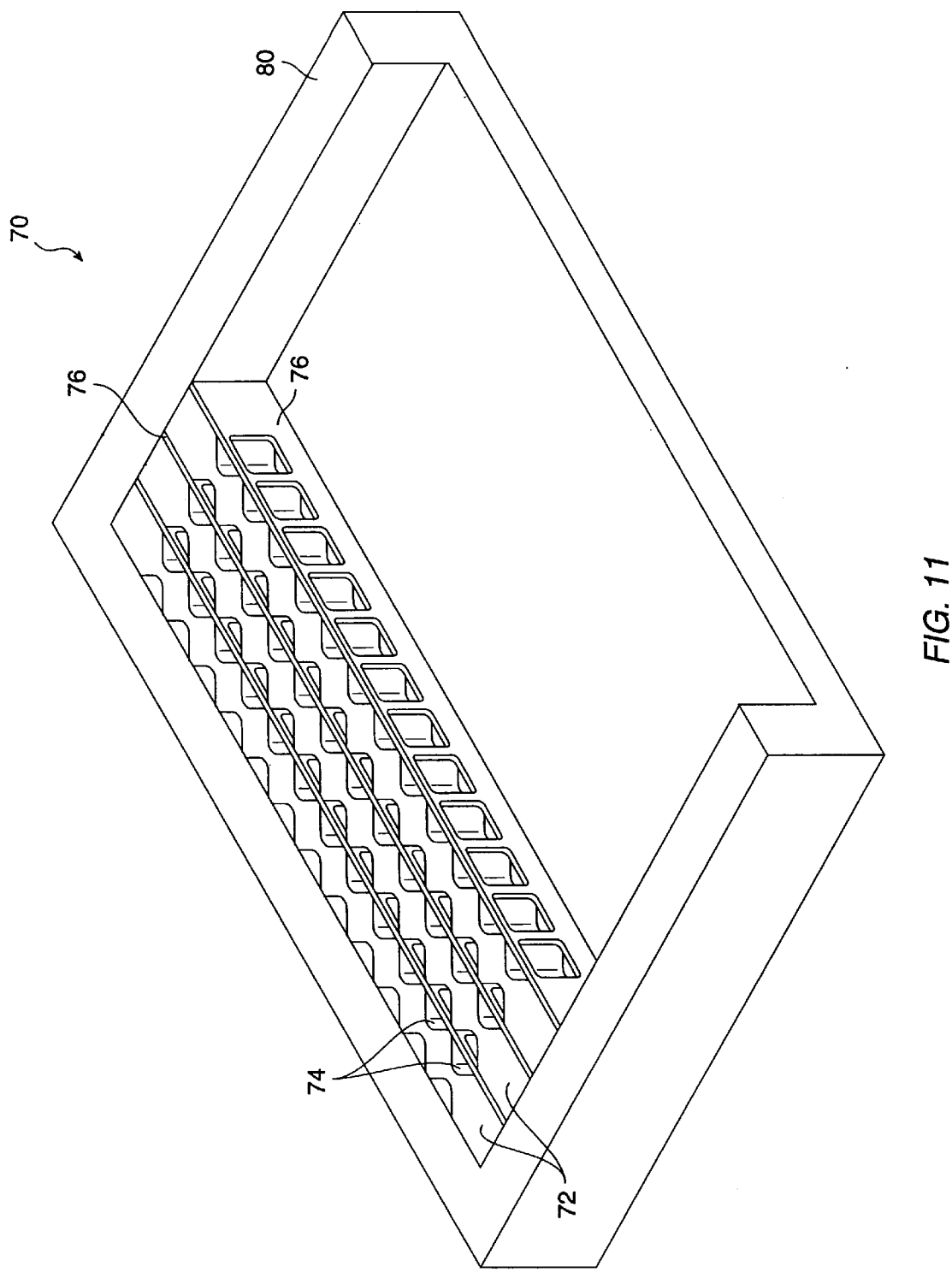
FIG. 11 is a perspective view of a further embodiment of a multi-well plate according to the invention.
Figure 12:
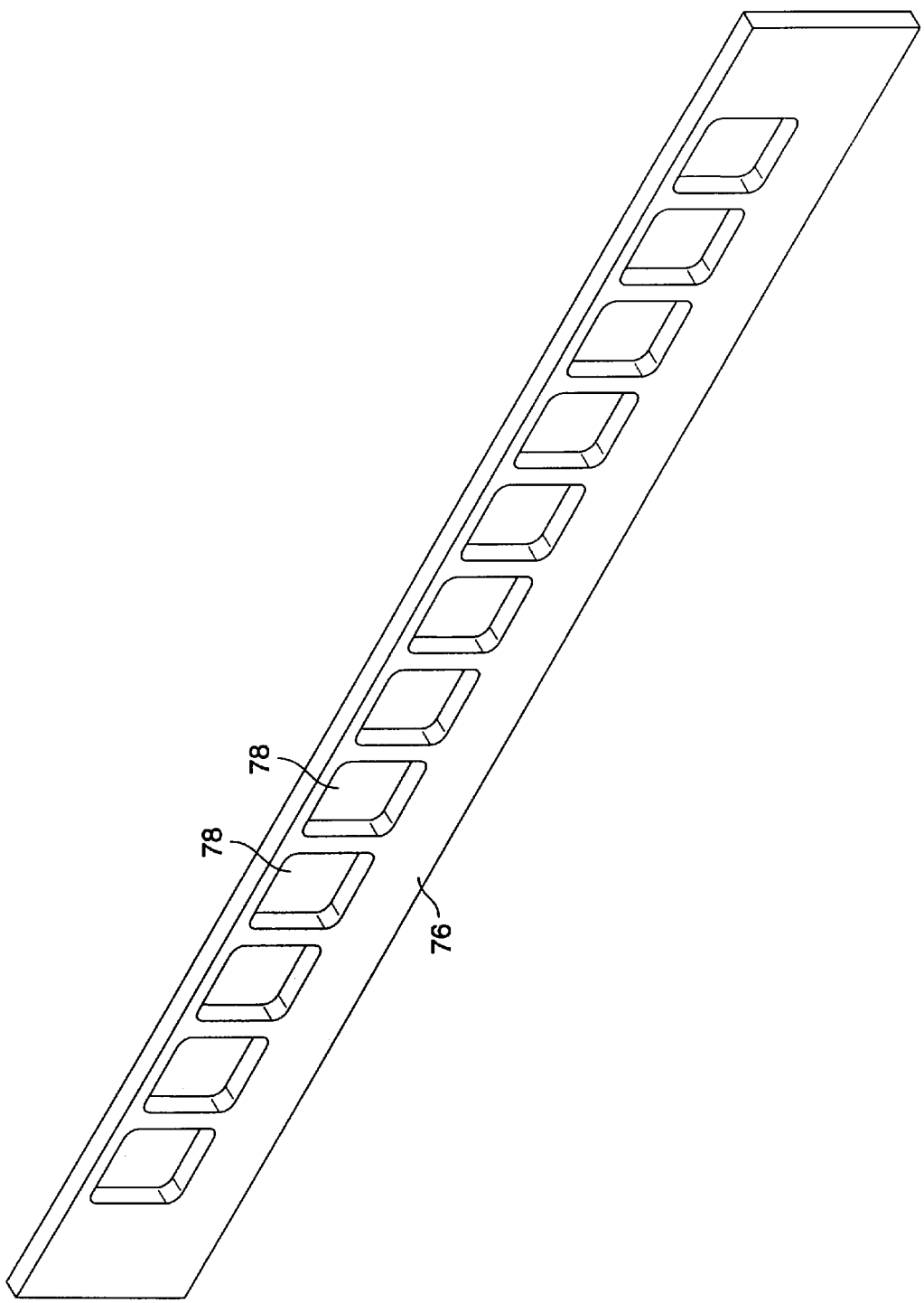
FIG. 12 is a perspective view of a section of the plate of FIG. 11.
Figure 13:
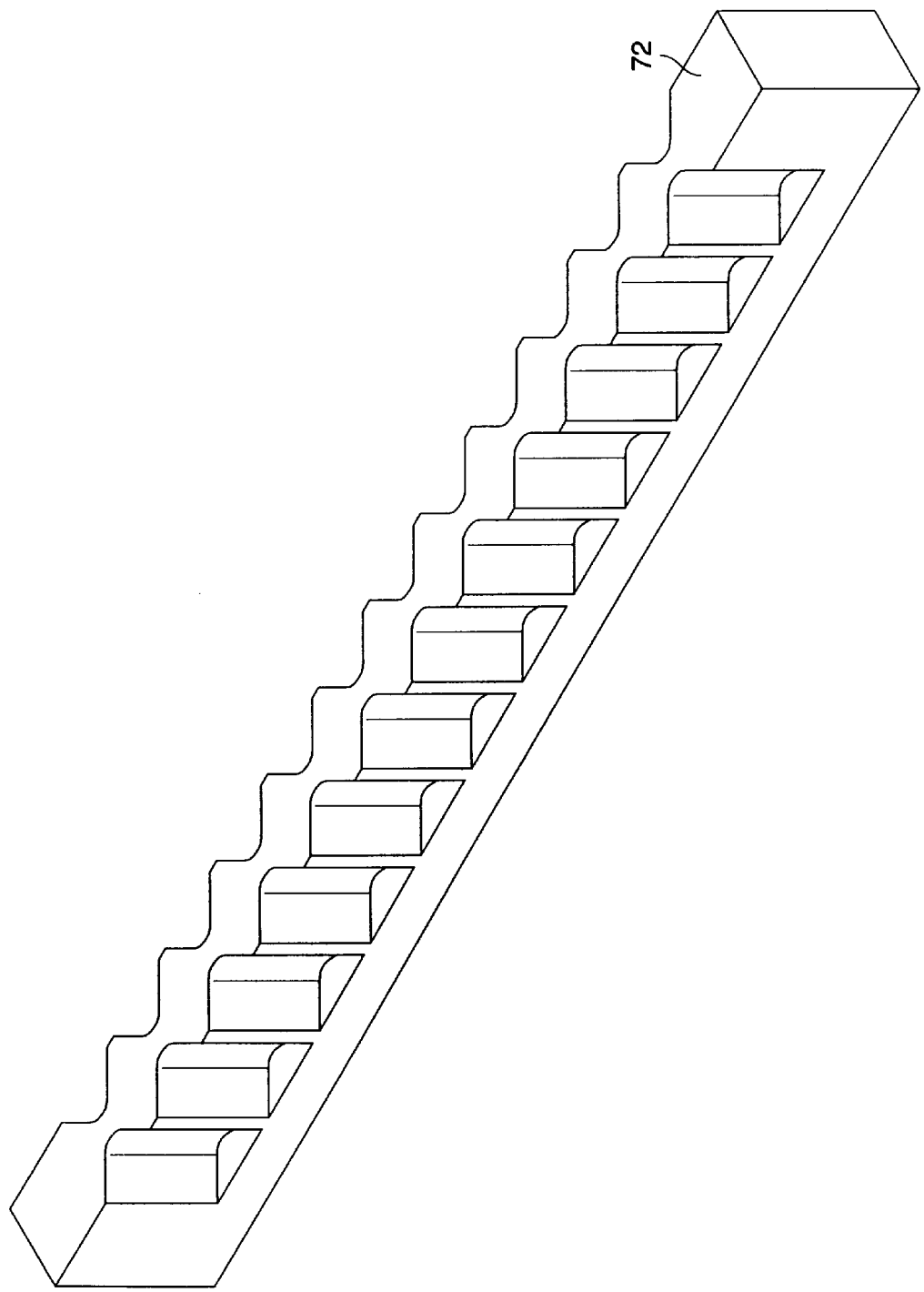
FIG. 13 is a perspective view of a divider for use with the plate of FIG. 11.

A modification of plate 42 is illustrated in FIG. 11 and is identified by reference numeral 70. Plate 70 is formed of a plurality of sections 72 which are placed together to form a plurality of wells 74. As best shown in FIG. 12, section 72 includes two rows of half-wells which are arranged so that when the sections are positioned adjacent each other, wells 74 will be formed as shown in FIG. 11. A divider 76 which is similar to the other dividers as previously described is positioned between two of the sections 72 as shown in FIG. 11 to divide the wells into separate chambers in a manner similar to that described with other embodiments. As best shown in FIG. 13, divider 76 includes a plurality of membranes 78 to which cells may be grown similar to other embodiments described herein.

One advantage of plate 70 is that it may be placed in a housing 80 (see FIG. 11) which services to align sections 72 and dividers 76 in their proper arrangement. Further, once in place, a clamp or other securing device (not shown) is employed to squeeze or force the sections 72 together. In this way, a tight seal will be provided between the sections and the dividers to prevent liquids from leaking from the wells. Hence, with this configuration, permeation tests may be performed without having the liquids leaking from the wells.

Figure 14:
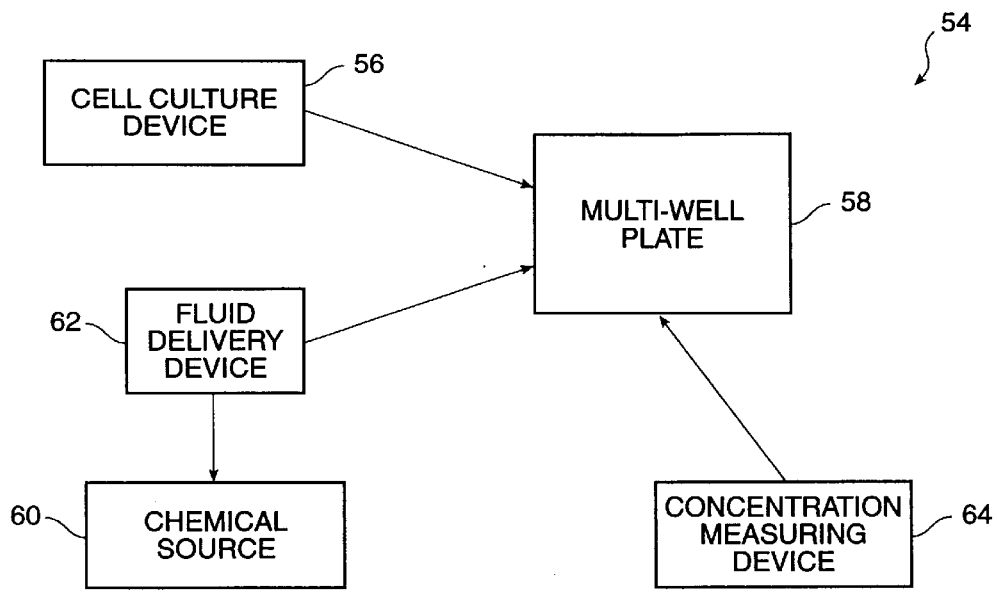
FIG. 14 is a schematic view of an exemplary system for performing permeation tests according to the invention.

Referring now to FIG. 14, an exemplary system 54 for testing the permeation or transport of a substance across a cell layer will be described. System 54 includes a cell culture device 56 which is employed to produce monolayers of epithelial cells, such as Caco-2 (Colon Carcinoma) or MDCK (Canine Kidney). Such cells in turn are used with the present invention as a model to study passive drug absorption across the intestinal epithelium in vitro. The confluent monolayers are subcultured whenever required by treatment with trypsin, EDTA and Phosphate-buffered saline (PBS). These cultures are maintained in a sterile environment within device 56 and incubated at 37 degrees C in a humidified atmosphere at 5% $CO^2$ 95% air.

When the cells are ready to be placed onto the membrane, the membrane is arranged in a horizontal orientation. The trypsinized cells are then seeded as epithelial layers onto the membrane. Any of the membrane configurations previously described herein may be used to receive the cells.

System 54 further includes a multi-well plate 58 which may be configured to be similar to any of the multi-well plates previously described herein. Multi-well plate 58 is configured to receive the membranes after the cells from cell culture device 56 have been seeded onto the membranes. The membranes are preferably arranged in a vertical orientation (although other orientations may be used) within plate 58 to separate the wells into a donor chamber and a receptor chamber as previously described. System 54 further includes a chemical source 60 which contains a chemical that is to be tested within plate 58. Exemplary chemicals which may be tested include a wide variety of drug compounds which would require transport across epithelial cells.

To deliver the chemicals from source 60 to the wells of plate 58, a fluid delivery device 62 is provided. Fluid delivery device 62 may comprise, for example, a single pipette, a multi-channel pipette, or an automated multichannel pipetting system that takes chemicals from source 60 and places them into the donor chambers of plate 58. To facilitate the testing procedure, each of the wells may be provided with a buffer solution into which the chemical is placed.

After the chemical has had a chance to diffuse into the receptor chamber, concentration measurements for the chemical are taken in both the donor chamber and the receptor chamber with a concentration measuring device 64. Such a concentration measuring device may comprise, for example, an HPLC, a fluorescent plate reader, an absorbance plate reader, and the like. The concentration measurements will preferably be taken over time so that the permeation rate of the chemical through the cell layer may be determined.

Figure 15:
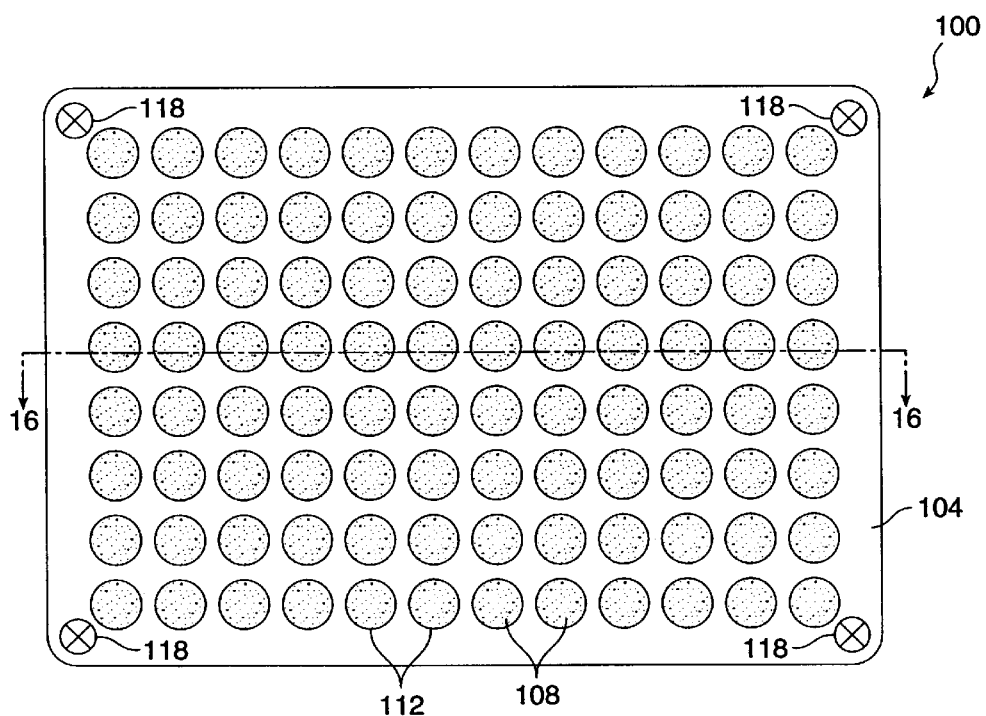
FIG. 15 is a top view of another exemplary testing system according to the invention.
Figure 16:
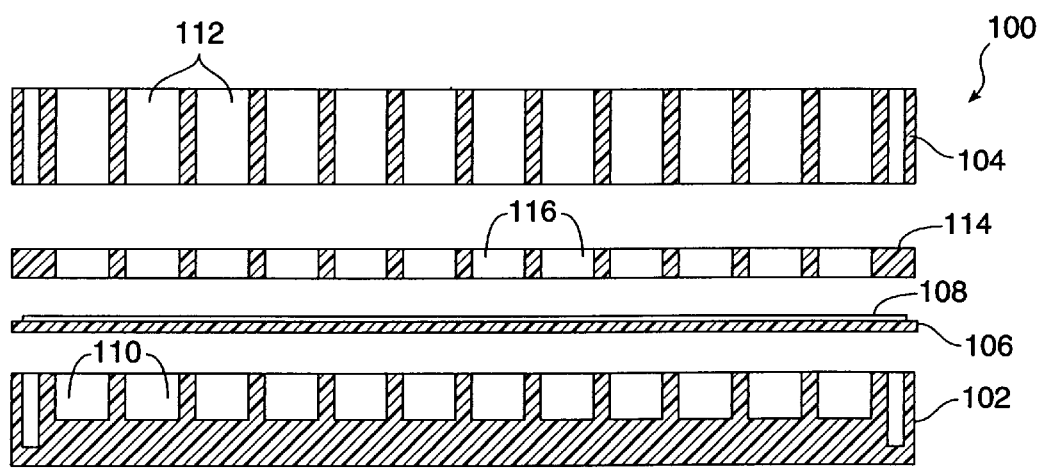
FIG. 16 is a exploded cross-sectional side view of the system of FIG. 15 taken along lines 16—16.

Referring now to FIGS. 15 and 16, an exemplary testing system 100 for measuring the apparent permeability values of compounds through monolayers of cells that are immobilized on a membrane in a high throughput manner will be described. System 100 comprises a base member 102, a top member 104 and a membrane sheet 106. Membrane sheet 106 includes at least one layer of cells 108 which are preferably grown on membrane sheet 106 prior to being placed between base member 102 and top member 104.

Base member 102 includes a plurality of wells 110 which are aligned with a plurality of apertures 112 within top member 104 when top member 104 is aligned with and secured to base member 102.

Optionally provided is a gasket 114 having a plurality of apertures 116 which correspond to apertures 112 of top member 104 to assist in providing an appropriate seal between top member 104 and base member 102 when secured together. A variety of securing mechanisms and devices may be employed to secure top member 104 to base member 102, such as, for example, clamps, screws, and the like. For instance, as illustrated in FIG. 15, a plurality of screws 118 extend through top member 104 to hold top member 104 to base member 102. Top member 104 and based member 102 will preferably include flat surfaces so that an adequate seal will be provided to prevent liquids from leaking from apertures 112 or wells 110.

Membrane sheet 106 will preferably constructed of a porous material, such as polycarbonate, PTFE, and the like. Membrane sheet 106 is removable from the system so as to allow cells to be grown onto the sheet to confluency, preferably as determined by their transepithelial electrical resistance (TEER) or impermeability to appropriate marker compounds (e.g., lucifer yellow).

Base member 102 will preferably include 96 wells which are arranged in a conventional format so that system 100 may be used with standard tools designed for use with 96 well micotiter dishes. For example, by arranging system 100 in this manner it may be readily integrated into a robotocized platform which performs compound addition, sampling, and analysis manipulations. However, it will appreciated that other numbers of wells and format types may be employed within the principles of the present invention.

In use, cells are preferably grown onto membrane sheet 106 as previously described in this application. Wells 110 of base member 102 are then preferably filled with an appropriate transport buffer solution. When system 100 is used in a horizontal orientation, each of wells 110 will preferably be filled to capacity. If used in a vertical orientation, wells 110 may be filled to less than capacity.

Membrane sheet 106 containing cells 108 is then inserted between base member 102 and top member 104 as illustrated in FIG. 16. Members 102 and 104 are then secured together so as to form a junction to prevent liquids from leaking around membrane 106. When appropriately secured together, apertures 112 are filled with a buffer containing an appropriate test compound or compounds.

For testing in the horizontal orientation, system 100 is placed at an appropriate temperature for a desired length of time. Optionally, system 100 may be shaken during the testing procedure. The solution within apertures 112 is then removed and each aperture 112 is washed and aspirated to remove any residual compound. The solutions within cells 110 are then evaluated to determine the concentration of the test compound that has permeated through membrane sheet 106. Access to wells 110 may be accomplished by puncturing membrane sheet 106, e.g., with a pipette, or by disassembling system 100. For testing in the vertical orientation, a cover will preferably be placed over apertures 112 to prevent spillage of their contents. Testing then proceeds as previously described for the horizontal orientation.

Based on the concentration of the substance within wells 110, the apparent permeability of the compounds through cells 108 may be determined. By providing a large number of wells, system 100 facilitates the ability to conduct permeation studies with multiple compounds simultaneously. Further, when the wells are arranged in a standard format, standard tools designed for use with 96 well microtiter plates may be employed. Arrangement of wells 110 is further advantageous in that testing may occur with considerably less compounds than has been required with other approaches. Further, by constructing membrane sheet 106 to be removable, the cell monolayers may be prepared in an efficient manner to further facilitate the testing procedure.

While system 100 has been illustrated in a 96 well format, it will be appreciated that a variety of well shapes, geometries, sizes, and the like may be employed within the principles of the invention. System 100 may optionally contain electrodes for determining TEER values. Further, sampling portions may be provided to facilitate sample addition and removal. Temperature control capabilities could also be provided to monitor and control the temperature during the testing procedure.

The invention has now been described in detail. However, it will be appreciated that certain changes and modifications may be made. Therefore, the scope and content of this invention are not limited by the foregoing description. Rather, the scope and content are to be defined by the following claims.

What is claimed is:

1. A testing device comprising:

a plate defining a plurality of wells;

an array of membranes which are insertable into the wells in a generally vertical orientation, whereby cells may be grown onto the membranes prior to insertion into the wells; and a divider to which the membranes are operably attached, the divider being insertable into the wells to hold the membranes in a generally vertical orientation within the wells.

2. A device as in claim 1, wherein the membranes are insertable into an open top end of the wells in a generally vertical orientation, and wherein the cells comprise mammalian-based cells.

3. A device as in claim 1, wherein the divider encompasses a periphery of the membranes.

4. A device as in claim 3, wherein the divider forms a raised edge around the periphery of the membranes to constrain cell growth to the membranes.

5. A device as in claim 1, wherein each well includes at least one generally vertically oriented slot into which the divider is received.

6. A device as in claim 1, wherein the divider comprises a plurality of teeth to which the membranes are operably attached and a bridge interconnecting the teeth, wherein the teeth are insertable into the array of wells to place a separate membrane into each well.

7. A device as in claim 1, wherein the divider comprises an elongate member to which the membranes are operably attached, wherein the plate includes an elongate slot extending between the array of wells, and wherein the elongate member is insertable into the slot to place the membranes into the wells.

8. A device as in claim 1, wherein the array is a two-dimensional array, with the wells being arranged in rows and columns, and further comprising a plurality of row dividers, each having a plurality of membranes operably attached thereto for insertion into each row of wells.

9. A device as in claim 1, wherein the membranes are constructed from the group of materials consisting of polytetrafluroethylene, polyethylene, PET and polycarbonate.

10. A method for performing assays, the method comprising:

providing a divider having a plurality of membranes;

inserting the divider into a plurality of wells in a generally vertical orientation so that each well includes one of the membranes to divide each well into a donor chamber and a receptor chamber;

growing cells onto the membranes; and introducing at least one substance into each donor chamber and allowing at least some of the substance to diffuse through the membranes and into the receptor chambers; and evaluating a characteristic of the substance that is within each donor chamber and each receptor chamber.

11. A method as in claim 10, wherein the evaluated characteristic comprises the concentration of the substance.

12. A method as in claim 10, wherein the evaluated characteristic comprises determining the permeation rate of the substance across each membrane.

13. A method as in claim 12, further comprising determining the permeation rate of the substance through the cells on the membranes based at least in part on the concentration of the substance within the donor chamber and the receptor chamber over time.

14. A method as in claim 10, wherein the substance comprises a chemical, and further comprising introducing a buffer solution into the chambers prior to placing the chemical into the donor chambers.

15. A method as in claim 10, further comprising seeding the cells onto the membranes while the membranes are in a generally horizontal orientation, and placing the membrane into the well in a generally vertical orientation.

16. A method as in claim 15, further comprising growing the cells onto the membranes prior to placement into the wells.

17. A method as in claim 15, further comprising growing the cells onto the membranes after placement into the wells.

18. A method as in claim 15, further comprising constraining the growth of the cells onto the membranes.

19. A method as in claim 10, wherein each well includes at least one generally vertically oriented slot, and further comprising sliding the divider through the slots when inserting the divider into the wells.

20. A method as in claim 10, wherein the divider comprises a plurality of teeth to which the membranes are operably attached and a bridge interconnecting the teeth, and further comprising inserting the teeth into an array of the wells to place a separate membrane into each well.

21. A method as in claim 10, wherein the divider comprises an elongate member to which the membranes are operably attached, wherein a plate having the wells includes an elongate slot extending between an array of the wells, and further comprising inserting the elongate member into the slot to place the membranes into the wells.

22. A method as in claim 10, wherein the wells are arranged in a two-dimensional array, with the wells being arranged in rows and columns, further comprising a plurality of row dividers, each having a plurality of membranes operably attached thereto, and further comprising inserting one divider into each row of wells.

23. A testing device comprising:

a plate defining at least one well; and at least one membrane which is insertable into the well;

a divider to which the membrane is operably attached, the divider being insertable into the well to hold the membrane in a generally vertical orientation within the well; and wherein the well includes at least one generally vertically oriented slot into which the divider is received.

* * * * *